US011118978B2

(12) United States Patent
Yang et al.

(10) Patent No.: US 11,118,978 B2
(45) Date of Patent: Sep. 14, 2021

(54) TEMPERATURE MEASURING DEVICE AND MEASUREMENT ALIGNMENT METHOD THEREOF

(71) Applicant: AVITA CORPORATION, New Taipei (TW)

(72) Inventors: Ta Chieh Yang, New Taipei (TW); Hsuan Hao Shih, New Taipei (TW); Hsing Ou Yang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 319 days.

(21) Appl. No.: 16/120,163

(22) Filed: Aug. 31, 2018

(65) Prior Publication Data

US 2019/0063997 A1 Feb. 28, 2019

(30) Foreign Application Priority Data

Aug. 31, 2017 (TW) .................. 106129626

(51) Int. Cl.
*G01J 5/02* (2006.01)
*A61B 5/00* (2006.01)
(Continued)

(52) U.S. Cl.
CPC .......... *G01J 5/0275* (2013.01); *A61B 5/7221* (2013.01); *G01J 5/0022* (2013.01); *G01J 5/0025* (2013.01);
(Continued)

(58) Field of Classification Search
CPC ...... G01J 5/0275; G01J 5/0022; G01J 5/0025; G01J 5/025; G01J 5/0265;
(Continued)

(56) References Cited

U.S. PATENT DOCUMENTS 6,129,673 A * 10/2000 Fraden ............. G01J 5/04
374/E13.003
6,196,714 B1 * 3/2001 Bellifemine ........ G01J 5/04
374/120
(Continued)

FOREIGN PATENT DOCUMENTS

CN 1284162 2/2001
JP 2015029881 2/2015
(Continued)

*Primary Examiner* — Nathaniel T Woodward
*Assistant Examiner* — Philip L Cotey
(74) *Attorney, Agent, or Firm* — Raymond Y. Chan; David and Raymond Patent Firm (57) ABSTRACT

A temperature measuring device includes at least one first distance sensing unit and a second distance sensing unit for outputting first and second distance sensing signals, respectively; a temperature sensing unit for outputting a temperature sensing signal; a display unit for displaying the temperature measurement value; and a micro processing unit for receiving the first and the second distance sensing signals, and then determining, according to the first and the second distance sensing signals, whether the display unit displays the temperature measurement value calculated according to the temperature sensing signal. As a result, the at least two distance sensing units are used to prevent the temperature measuring device from executing the temperature measurement when the sensing unit of the thermometer obliquely points to a to-be-sensed part of a to-be-measured target to cause a large measurement angle.

12 Claims, 6 Drawing Sheets

(51) Int. Cl.
*G01J 5/00* (2006.01)
*G01K 13/20* (2021.01)

(52) U.S. Cl.
CPC ............. *G01J 5/025* (2013.01); *G01J 5/0265* (2013.01); *G01K 13/223* (2021.01); *G01J 2005/0048* (2013.01)

(58) Field of Classification Search
CPC ............. G01J 2005/0048; A61B 5/742; A61B 5/7221; G01K 5/22; G01K 13/004
See application file for complete search history.

(56) References Cited

U.S. PATENT DOCUMENTS

| | | | | |
|---|---|---|---|---|
| 7,056,012 | B2 * | 6/2006 | Blakeley, III | G01J 5/041 374/120 |
| 2003/0099277 | A1 * | 5/2003 | Bellifemine | G01J 5/089 374/121 |
| 2006/0050766 | A1 * | 3/2006 | Hollander | G01J 5/0893 374/121 |
| 2007/0191729 | A1 * | 8/2007 | Park | A61B 5/107 600/551 |
| 2008/0246625 | A1 * | 10/2008 | Chen | G01J 5/0025 340/686.6 |
| 2008/0259730 | A1 * | 10/2008 | Di Federico | G01J 5/041 367/118 |
| 2009/0182526 | A1 * | 7/2009 | Quinn | G01J 5/0806 702/131 |
| 2011/0216806 | A1 * | 9/2011 | Weng | G01J 5/00 374/128 |
| 2013/0018626 | A1 * | 1/2013 | Chi | G01J 5/0275 702/135 |
| 2013/0195141 | A1 * | 8/2013 | Koudo | G01J 5/00 374/170 |
| 2014/0046192 | A1 * | 2/2014 | Mullin | H05K 13/00 600/474 |
| 2016/0113517 | A1 * | 4/2016 | Lee | H04M 1/72522 600/474 |
| 2016/0156856 | A1 * | 6/2016 | Lee | G01J 5/00 348/164 |
| 2016/0157732 | A1 * | 6/2016 | Tanaka | G01J 5/0275 600/474 |
| 2016/0316154 | A1 * | 10/2016 | Elmfors | G01J 5/0834 |
| 2018/0313695 | A1 * | 11/2018 | Shim | G06K 9/2018 |

FOREIGN PATENT DOCUMENTS

| | | |
|---|---|---|
| TW | I572326 | 3/2017 |
| WO | WO2011113727 | 9/2011 |

* cited by examiner

TEMPERATURE MEASURING DEVICE AND MEASUREMENT ALIGNMENT METHOD THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a temperature measuring device and a method thereof. More particularly, the present invention relates to a temperature measuring device with measurement alignment function, and a method thereof.

Description of Related Arts

In recent years, the traditional contact thermometers, such as mercury or electronic thermometers, can no longer meet the needs of users, so there is a need to develop a temperature measuring method and device to provide accurate, fast, simple, easy-to-interpret, no-harm, and human-friendly temperature measurement. A non-contact temperature measuring device for measuring infrared radiant heat, for example, an ear thermometer or a forehead thermometer, which has above advantages and gradually becomes a mainstream body temperature measuring device. Furthermore, the infrared thermometer can measure the temperature of a red-hot object, a dangerous object, or a hard-to-reach object by a non-contact manner.

When using the infrared thermometer, the user can align a sensing unit of the infrared thermometer to a target to be measured and then press a button switch of the infrared thermometer, so as to measure the temperature of the target in a non-contact manner. Generally, during the process of measuring temperature, the distance between the sensing unit of the infrared thermometer and the to-be-measured target may be different for every measurement, so that the measured temperature value may have error because of the different measured distance, and it also causes measurement uncertainty. Taiwan Patent No. 1351942 discloses a temperature measuring device using a single position sensing unit for sensing the distance, so as to determine whether to execute temperature measurement according to the sensed distance; however, the temperature measuring device does not calculate the temperature value in consideration of the distance sensed by the position sensing unit.

Furthermore, the angle by which the sensing unit of the infrared thermometer points to a to-be-sensed part of the target, may also affect the temperature measurement result. If the pointing operation is skewed or deflected to cause a too large angle, the operation of the sensing unit to continuously receive energy of the reflected light beam may be affected and thus impact the calculation of accurate temperature value.

SUMMARY OF THE PRESENT INVENTION

An objective of the present invention is that at least two distance sensing units are used to prevent the temperature measurement from being performed when the measurement angle by which the sensing unit of the thermometer obliquely points to the to-be-sensed part of the to-be-measured target is too large.

Another objective of the present invention is that at least two distance sensing units are used to evaluate a measurement angle of the to-be-sensed part, and the temperature measuring device can calculate a temperature measurement value with an acceptable accuracy according to a temperature sensing signal, within a tolerable measurement angle or range; or, the temperature measuring device can calculate a more accurate temperature measurement value according to the temperature sensing signal and the measurement angle of the to-be-sensed part.

In order to achieve the objectives, the present invention provides a temperature measuring device comprising at least one first distance sensing unit and a second distance sensing unit, a temperature sensing unit, a display unit, and a micro processing unit. The first distance sensing unit and the second distance sensing unit are configured to output a first distance sensing signal and a second distance sensing signal, respectively. The temperature sensing unit is configured to output a temperature sensing signal. The display unit is configured to display a temperature measurement value. The micro processing unit is electrically connected to the first distance sensing unit, the second distance sensing unit, the temperature sensing unit, and the display unit, and is configured to receive the first distance sensing signal and the second distance sensing signal, and determine, according to the first distance sensing signal and the second distance sensing signal, whether the display unit displays the temperature measurement value calculated according to the temperature sensing signal.

Preferably, the micro processing unit determines, according to association between the first distance sensing signal, the second distance sensing signal and a measurement execution condition, whether the display unit displays the temperature measurement value calculated according to the temperature sensing signal.

Preferably, the measurement execution condition comprises a first predetermined signal and a second predetermined signal, or a first predetermined signal range and a second predetermined signal range, or a first predetermined value and a second predetermined value, or a first predetermined range and a second predetermined range.

Preferably, the temperature measuring device further comprises a correspondence table recording a first sensed distance, a second sensed distance and a measurement angle, and the first sensed distance and the second sensed distance are calculated according to the first distance sensing signal and the second distance sensing signal, respectively, and the measurement execution condition is the correspondence table.

Preferably, the micro processing unit obtains the measurement angle corresponding to the first sensed distance and the second sensed distance from the correspondence table, and calculate the temperature measurement according to the temperature sensing signal and the searched measurement angle.

Preferably, the first distance sensing unit, the second distance sensing unit and the temperature sensing unit are positioned on an axis.

Preferably, the temperature measuring device further comprises a third distance sensing unit electrically connected to the micro processing unit and configured to output a third distance sensing signal, wherein the micro processing unit determines, according to the first distance sensing signal, the second distance sensing signal and the third distance sensing signal, whether the display unit displays the temperature measurement value calculated according to the temperature sensing signal Preferably, the first distance sensing unit and the temperature sensing unit are positioned on an axis, and the second distance sensing unit and the third distance sensing unit are symmetrically positioned on two sides of the axis.

Preferably, the micro processing unit determines, according to association between the first distance sensing signal, the second distance sensing signal, the third distance sensing signal and a measurement execution condition, whether the display unit displays the temperature measurement value calculated according to the temperature sensing signal.

Preferably, the temperature measuring device further comprises a correspondence table recording a first sensed distance, a second sensed distance, a third sensed distance and a measurement angle, and the first sensed distance, the second sensed distance, and the third sensed distance are calculated according to the first distance sensing signal, the second distance sensing signal and the third distance sensing signal, respectively, and the measurement execution condition is the correspondence table.

Preferably, the micro processing unit obtains the measurement angle corresponding to the first sensed distance, the second sensed distance and the third sensed distance from the correspondence table, and calculate the temperature measurement according to the temperature sensing signal and the searched measurement angle.

In order to achieve the objectives, the present invention provides a measurement alignment method applied to a temperature measuring device, and the temperature measuring device comprises a display unit for displaying a temperature measurement value. The method comprises steps of disposing at least one first distance sensing unit and a second distance sensing unit; enabling a first distance sensing unit and a second distance sensing unit, to obtain a first distance sensing signal and a second distance sensing signal; and determining whether the display unit displays the temperature measurement value, according to the first distance sensing signal and the second distance sensing signal.

Preferably, the measurement alignment method further comprises steps of comparing the first distance sensing signal, the second distance sensing signal and a measurement execution condition, to determine whether the display unit displays the temperature measurement value calculated according to the temperature sensing signal.

Preferably, the measurement execution condition comprises a first predetermined signal and a second predetermined signal, or a first predetermined signal range and a second predetermined signal range, or a first predetermined value and a second predetermined value, or a first predetermined range and a second predetermined range.

Preferably, the measurement alignment method further comprises steps of providing a correspondence table recording a first sensed distance, a second sensed distance and a measurement angle, and the first sensed distance and the second sensed distance are calculated according to the first distance sensing signal and the second distance sensing signal, respectively, and the measurement execution condition is the correspondence table, and the measurement angle corresponding to the first and second sensed distances can be searched from the correspondence table, and the temperature measurement can be calculated according to the temperature sensing signal and the measurement angle corresponding thereto.

Preferably, the measurement alignment method further comprises steps of positioning the first distance sensing unit and the second distance sensing unit on an axis.

Preferably, the measurement alignment method further comprises steps of disposing a third distance sensing unit; enabling the third distance sensing unit to obtain a distance sensing signal; and, determining whether the display unit displays the temperature measurement value, according to the first distance sensing signal, the second distance sensing signal and the third distance sensing signal.

Preferably, the measurement alignment method further comprises steps of positioning the second distance sensing unit and the third distance sensing unit symmetrically on two sides of an axis, and positioning the first distance sensing unit on the axis.

Preferably, the measurement alignment method further comprises steps of according to association between the first, second and third distance sensing signal and a measurement execution condition, to determine whether the display unit display the calculated temperature measurement value according to the temperature sensing signal.

Preferably, the measurement alignment method further comprises steps of providing a correspondence table recording a first sensed distance, a second sensed distance, a third sensed distance and a measurement angle, wherein the first, second and third sensed distances are calculated according to the first, second and third distance sensing signals, respectively, and the measurement execution condition is the correspondence table; and, searching the measurement angle corresponding to the first, second and third sensed distances from the correspondence table, and the calculating the temperature measurement according to the temperature sensing signal and the measurement angle corresponding thereto.

When using the temperature measuring device and the measurement alignment method of the present invention, the user can evaluate the measurement angle of the to-be-sensed part of the to-be-measured target to which the sensing unit points, according to the distance sensing results of the at least two distance sensing units, so as to prevent from inaccurate temperature measurement because the temperature measurement angle is shifted when the user operates the thermometer. As a result, the temperature measurement result can be maintained as a temperature measurement value with acceptable accuracy; furthermore, the temperature measuring device of the present invention can calculate the more accurate temperature measurement value in consideration of the effect of the measurement angle of the to-be-sensed part.

BRIEF DESCRIPTION OF THE DRAWINGS

The structure, operating principle and effects of the present invention will be described in detail by way of various embodiments which are illustrated in the accompanying drawings.

DETAILED DESCRIPTION OF THE PREFERRED EMBODIMENT

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be understood that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the word "comprise" and variations such as "comprises" or "comprising", will be understood to imply the inclusion of stated elements but not the exclusion of any other elements.

Figure 1:
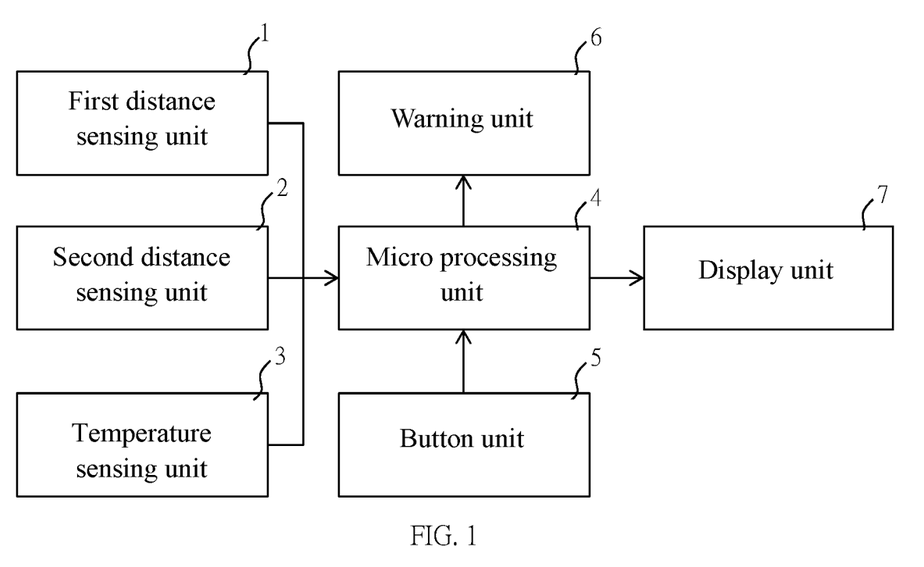
FIG. 1 is a block diagram of a temperature measuring device of an embodiment of the present invention.

Please refer to FIG. 1, which shows a block diagram of a temperature measuring device of the present invention. In this embodiment, the temperature measuring device includes a temperature sensing unit 3 configured to output a temperature sensing signal, a button unit 5 configured to generate a trigger signal, a display unit 7 configured to display a temperature measurement value, and a micro processing unit 4 electrically connected to the temperature sensing unit 3, the button unit 5 and the display unit 7. The micro processing unit 4 controls the temperature sensing unit 3 to execute temperature measurement, and receives the temperature sensing signal outputted by the temperature sensing unit 3, and then calculate the temperature measurement value. The micro processing unit 4 can control the display unit 7 and output the temperature measurement value to the display unit 7 for display. In an embodiment, the temperature sensing unit 3 is an infrared sensing unit, and the infrared sensing unit can be aligned and pointed to the to-be-measured target for performing non-contact temperature measurement. Preferably, the button unit 5 can be a pressing switch, and the user can operate the pressing switch by, for example, short press or long press, to generate different trigger signals to the micro processing unit 4, so that the micro processing unit 4 can execute the predetermined operation according to the received trigger signal. For example, the predetermined operations can include temperature and distance measurement operation, or power-on operation, or power-off operation. Preferably, the display unit 7 can be a liquid crystal display device. Furthermore, the micro processing unit 4 can include a built-in memory configured to store the calculated temperature measurement value, various data types of a measurement execution condition, or a correspondence table. The measurement execution condition or correspondence table are used in different embodiments of the measurement alignment method of the present invention.

The temperature measuring device can include a first distance sensing unit 1 and a second distance sensing unit 2 which are electrically connected to the micro processing unit 4 and configured to output a first distance sensing signal and a second distance sensing signal, respectively. The temperature measuring device can include a warning unit 6 electrically connected to the micro processing unit 4, and configured to receive the warning signal outputted by the micro processing unit 4. In an embodiment of the present invention, after the micro processing unit 4 receives the trigger signal generated by the button unit 5, the micro processing unit 4 enables one of the first distance sensing unit 1 and the second distance sensing unit 2 to execute the distance sensing operation, and then determines whether to enable the temperature sensing unit 3 to execute temperature measurement according to the distance sensing signal. In another embodiment of the present invention, the micro processing unit 4 enables the first distance sensing unit 1 to execute the distance sensing operation, and then determines whether to enable the second distance sensing unit 2 to perform the distance sensing operation, according to the first distance sensing signal, and then determines whether to enable the temperature sensing unit 3 to execute temperature measurement, according to the first distance sensing signal and the second distance sensing signal. Furthermore, after the micro processing unit 4 determines, according to at least one of the first distance sensing signal the second distance sensing signal, to execute the temperature measurement, the micro processing unit 4 outputs the warning signal to the warning unit 6, so as to prompt the user that the temperature measuring device is measuring temperature, and also prompt the user to not shift the temperature measuring device, thereby avoiding affecting the accuracy of the measured temperature. In an embodiment, the warning unit 6 can be a LED device or a buzzer.

In another embodiment of the present invention, the first distance sensing unit 1 can be a light transceiver unit, the second distance sensing unit 2 can be a receiving unit, and when the first distance sensing unit 1 emits light beam to the to-be-sensed part, the to-be-sensed part reflects the light beam, and the first distance sensing unit 1 and the second distance sensing unit 2 can receive the reflected light beam, and the micro processing unit 4 can determine, according to the measurement results of the first distance sensing unit 1 and the second distance sensing unit 2, whether to execute the distance sensing operation. In another embodiment of the present invention, the first distance sensing unit 1 is the light transceiver unit, the second distance sensing unit 2 is also the light transceiver unit, and when the first distance sensing unit 1 and the second distance sensing unit 2 emit light beams to the to-be-sensed part, respectively, the to-be-sensed part reflects the two light beams, and the first distance sensing unit 1 and the second distance sensing unit 2 can receive the two reflected light beams, respectively, and the micro processing unit 4 can determine, according to the measurement results of the first distance sensing unit 1 and the second distance sensing unit 2, whether to execute the distance sensing operation.

Figure 2:
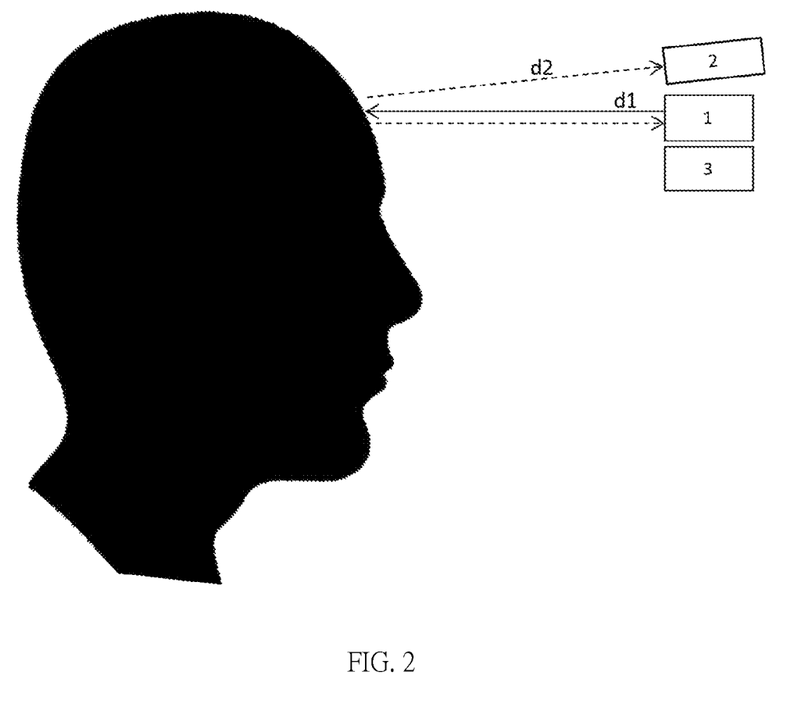
FIG. 2 is a schematic view showing an operation of the temperature measuring device points to the to-be-measured target for distance and temperature measurement, according to an embodiment of the present invention.

Please refer to FIG. 2, which shows a schematic view of an operation of the temperature measuring device is pointed to the to-be-measured target for sensing the distance and measuring temperature. In this embodiment, the temperature measuring device uses two distance sensing units 1 and 2 and the temperature sensing unit 3 to evaluate a measurement angle of the to-be-sensed part of the to-be-measured target to which the temperature sensing unit 3 is pointed. The first distance sensing unit 1, the second distance sensing unit 2 and the temperature sensing unit 3 are position on an axis. With configurations of the first distance sensing unit 1 and the second distance sensing unit 2, a measurement angle may be formed between optical paths of the first distance sensing unit 1 and the second distance sensing unit 2, that is, an included angle may be formed between the distances d1 and d2 shown in FIG. 2; and, optical paths of the first distance sensing unit 1 and the second distance sensing unit 2 may be parallel with each other, that is, the distances d1 and d2 are parallel with each other. The first distance sensing signal outputted from the first distance sensing unit 1 is a distance sensing result for the distance d1, and the second distance sensing signal outputted from the second distance sensing unit 2 is a distance sensing result for the distance d2, and the micro processing unit 4 can calculate the distances d1 and d2 according to the first and the second distance sensing signals. The first distance sensing signal and the second distance sensing signal, or the calculated distances d1 and d2 can be used to evaluate the measurement angle of the to-be-sensed part of the to-be-measured target to which the temperature sensing unit 3 points.

In embodiment an of the present invention, the memory of the micro processing unit 4 stores the measurement execution condition in advance, and the measurement execution condition is used to evaluate the first distance sensing signal and the second distance sensing signal outputted from the first and second distance sensing units 1 and 2, as shown in FIG. 2. In the process that the user operates the temperature measuring device of the present invention to execute temperature measurement, when the micro processing unit 4 determines that the first distance sensing signal and the second distance sensing signal outputted from the first and second distance sensing units 1 and 2 match the measurement execution condition, it indicates that the user operates the temperature measuring device of the present invention to measure temperature within a predetermined distance or a predetermined range, thereby preventing the accuracy of the measured temperature from being affected because the measurement angle of the to-be-sensed part is skewed excessively. In another embodiment of the present invention, the memory of the micro processing unit 4 can store the correspondence table in advance, and the correspondence table stores the measurement angle of the to-be-sensed part corresponding to the first distance sensing signal and the second distance sensing signal, or the calculated distance d1 and d2 within tolerable measurement angles or a tolerable measurement angle range. When the user operates the temperature measuring device of the present invention to execute temperature measurement, the micro processing unit 4 can determine, according to the correspondence table, whether the first distance sensing signal and the second distance sensing signal, or the calculated distances d1 and d2 are within the tolerable measurement angle or the tolerable range, and then determine whether to enable the temperature sensing unit 3 to execute temperature measurement to calculate a temperature measurement value with an acceptable accuracy. Further, the measurement angle of the to-be-sensed part can be obtained from the correspondence table according to the first distance sensing signal and the second distance sensing signal or the calculated distance d1 and d2, and the micro processing unit 4 can calculate a more accurate temperature measurement value according to the temperature sensing signal and the measurement angle of the to-be-sensed part.

Furthermore, as shown in FIG. 2, the distance sensing unit 1, the distance sensing unit 2, and the temperature sensing unit 3 are positioned on an axis, and in the measurement execution condition, the range of the distance d1, such as a range of 1 cm to 5 cm, is a distance range in which the measurement can be performed; and, when the distance d2 is higher than the distance d1, it indicates that the user holds the temperature measuring device by a downwardly-deflecting posture; and, when the distance d2 is lower than the distance d1, it indicates the temperature measuring device by an upwardly-deflecting posture. For this reason, within a preset range of distance d1, the range of a ratio of the distance d2 to the distance d1 can be used to define a tolerable measurement angle, and the different distances d1 and d2, and the tolerable measurement angle corresponding thereto can be collected in advance and recorded in the correspondence table for implementing the determination step 204 of FIG. 4, the determination step 304 of FIG. 5 and the determination step 404 of FIG. 6.

Figure 3:
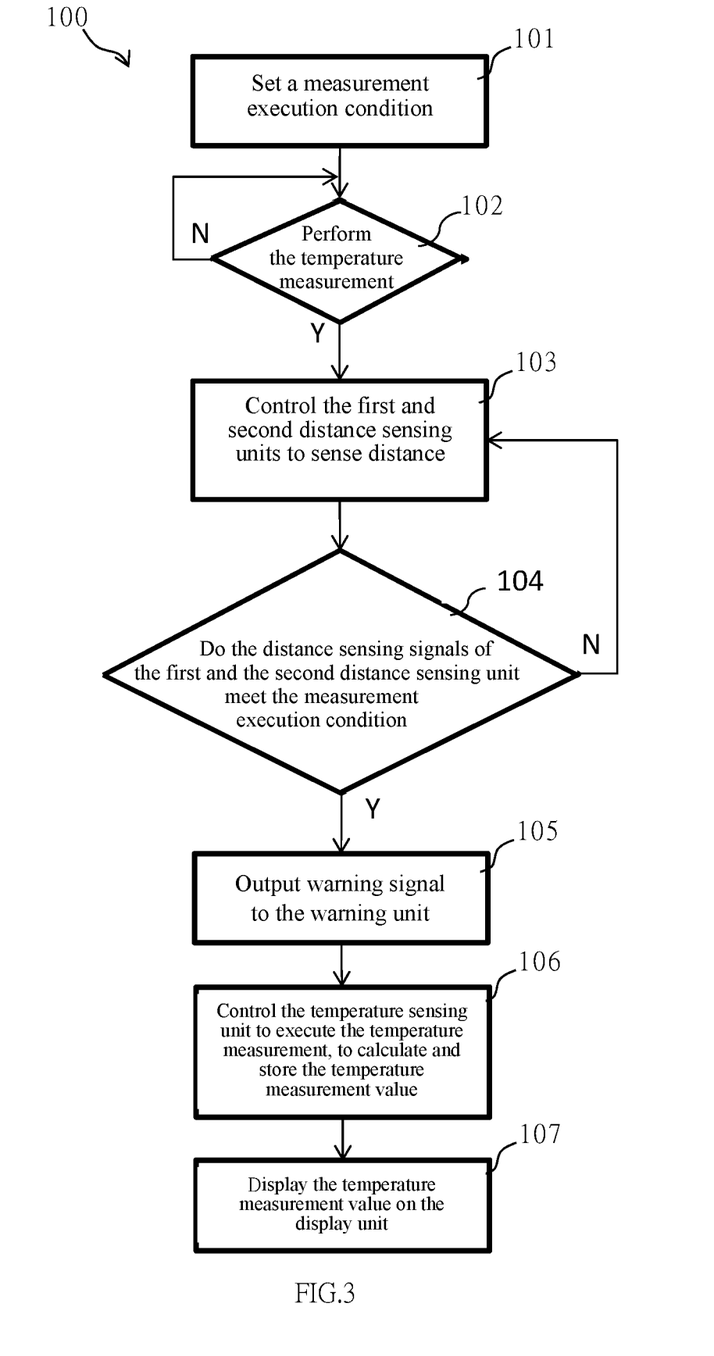
FIG. 3 is a flow chart of a first embodiment of a measurement alignment method of the present invention.

Please refer to FIG. 3, which shows a flow chart of a first embodiment of a measurement alignment method of the present invention. In this embodiment, a measurement alignment method 100 can be performed by using the temperature measuring device described above, and the measurement alignment method 100 comprises following steps. In a step 101, the micro processing unit 4 sets a measurement execution condition in advance, and the measurement execution condition can be used to evaluate the first distance sensing signal and the second distance sensing signal outputted from the first and second distance sensing units 1 and 2, as shown in FIG. 2; and, the measurement execution condition can be set in consideration of the first predetermined signal and the second predetermined signal which indicate the distance sensing signals outputted from the first and second distance sensing units 1 and 2 in the predetermined distances d1 and d2 shown in FIG. 2, respectively; or, the measurement execution condition can be set in consideration of a first predetermined signal range and a second predetermined signal range which indicate a variation range of the distance sensing signals outputted from the first and second distance sensing units 1 and 2 in an tolerable range of the predetermined distances d1 and d2 shown in FIG. 2, respectively; or, the measurement execution condition can be set in consideration of a first predetermined value and a second predetermined value which indicate the predetermined distances d1 and d2, as shown in FIG. 2, suitable for the first and second distance sensing units 1 and 2 to measure temperature; or, the measurement execution condition can be set in consideration of a first predetermined range and a second predetermined range which indicate a variation range of the predetermined distances d1 and d2, as shown in FIG. 2, suitable for the first and second distance sensing units 1 and 2 to measure temperature.

Please refer to FIG. 3. In a step 102, the micro processing unit 4 determines whether to execute the temperature measurement; for example, the micro processing unit 4 can determine according to the trigger signal of the button unit 5, when the button unit 5 is pressed to generate the trigger signal, the method proceeds a step 103; otherwise, the method proceeds the step 102 again. Furthermore, the micro processing unit 4 can determine, according to the distance sensing signal of one of the first and second distance sensing units 1 and 2, whether to execute the temperature measurement. For example, the first distance sensing unit 1 is taken as example, when the distance sensing signal outputted from the first distance sensing unit 1 is a distance sensing signal indicative of the predetermined distance d1, the method proceeds a step 103, otherwise, the method repeat the determination operation; or, the micro processing unit 4 can calculate the sensed distance according to the distance sensing signal outputted from the first distance sensing unit 1, and when the sensed distance is the predetermined distance d1, the method proceeds the step 103, otherwise, the method repeats the determination operation. In the step 103, the micro processing unit 4 controls the first and second distance sensing units 1 and 2 to sense distance, and receives the distance sensing signal outputted from the first and second distance sensing units 1 and 2.

Next, in a step 104, the micro processing unit 4 determines whether the distance sensing signals of the first and the second distance sensing unit meet the measurement execution condition, and if yes, the method proceeds a step 105; otherwise, the method proceeds the step 103 to continuously sense distance. The micro processing unit 4 performs determination according to different setting of the measurement execution condition. For example, when the measurement execution condition includes the first predetermined signal and the second predetermined signal, the micro processing unit 4 can determine whether the two distance sensing signals outputted from the first and second distance sensing units 1 and 2 are the same as the first predetermined signal and the second predetermined signal substantially, if yes, it indicates that the measurement execution condition is satisfied, otherwise, the measurement execution condition is not satisfied. When the measurement execution condition includes the first predetermined signal range and the second predetermined signal range, the micro processing unit 4 can determine whether the two distance sensing signals outputted from the first and second distance sensing units 1 and 2 are within the first predetermined signal range and the second predetermined signal range, respectively, if yes, it indicates that the measurement execution condition is satisfied; otherwise, the measurement execution condition is not satisfied. When the measurement execution condition includes the first predetermined value and the second predetermined value, the micro processing unit 4 can determine whether the two sensed distance calculated according to the two distance sensing signals outputted from the first and second distance sensing units 1 and 2, are substantially the same as the first predetermined value and the second predetermined value, and if yes, it indicates that the measurement execution condition is satisfied; otherwise, the measurement execution condition is not satisfied. When the measurement execution condition includes the first predetermined range and the second predetermined range, the micro processing unit 4 can determine whether the two sensed distances calculated according to the two distance sensing signals outputted from the first and second distance sensing units 1 and 2, are within the first predetermined range and the second predetermined range, respectively, and if yes, it indicates that the measurement execution condition is satisfied; otherwise, the measurement execution condition is not satisfied.

Next, in a step 105, the micro processing unit 4 outputs the warning signal to the warning unit 6, for prompting the user that the operation of the temperature measuring device is correct and further prompting the user to not shift the device, so as to avoid affecting the accuracy of the measured temperature. Preferably, the warning unit 6 can be the LED device or the buzzer. In a step 106, the micro processing unit 4 controls the temperature sensing unit 3 to execute the temperature measurement, to calculate and store the temperature measurement value. In a step 107, the micro processing unit 4 outputs the temperature measurement value to the display unit 7 for displaying the temperature measurement value. Furthermore, in this embodiment, the execution order of the step 105, the step 106, and the step 107 is not limited, and the step 105; and, the step 106, and the step 107 can be executed in any order as long as the warning unit 6 can prompt the user that the device is operated in the correct position after the micro processing unit 4 determines that the distance sensing signal of the first and the second distance sensing unit meet the measurement execution condition.

Figure 4:
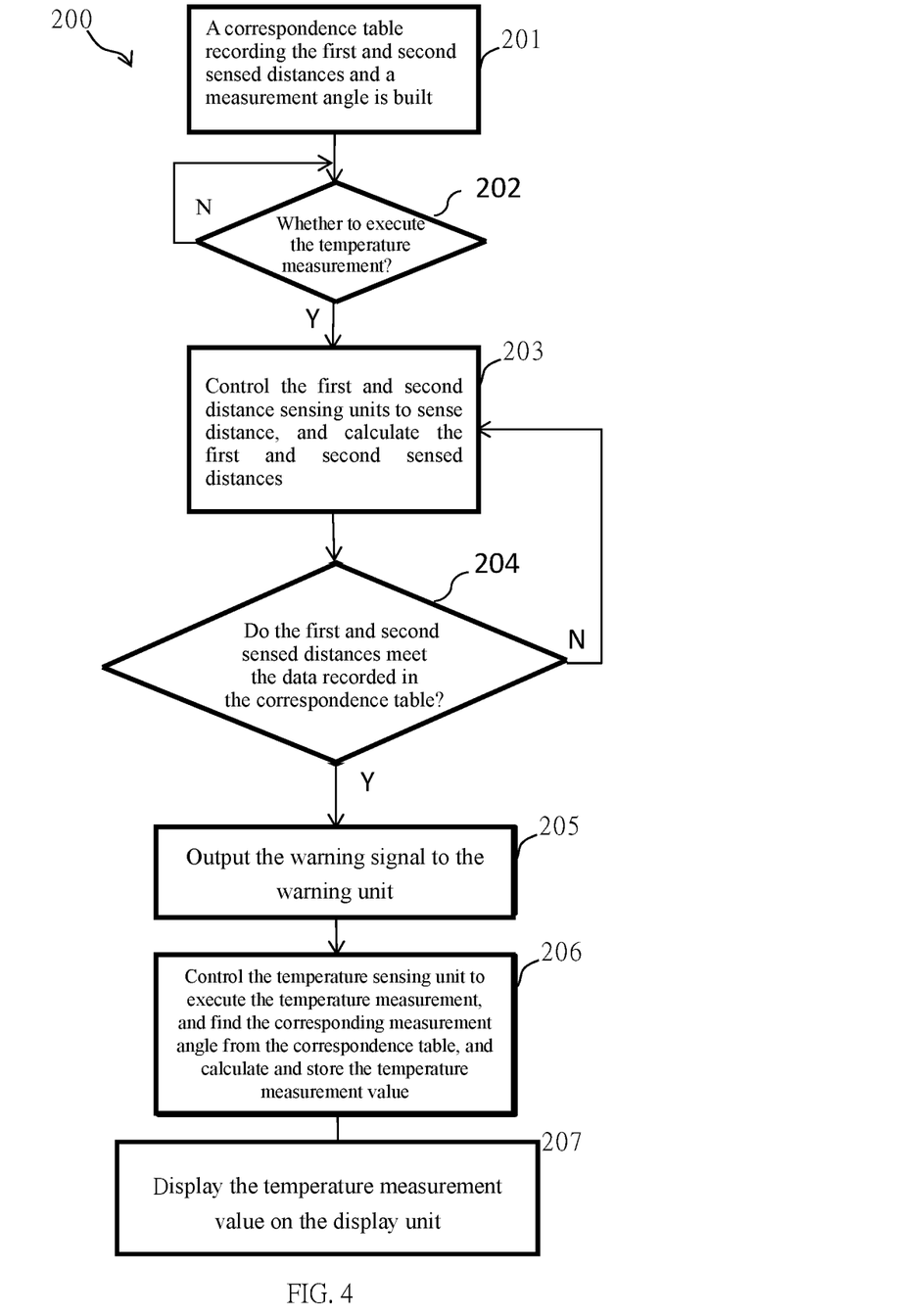
FIG. 4 is a flow chart of a second embodiment of a measurement alignment method of the present invention.

Please refer to FIG. 4, which shows a flow chart of a second embodiment of a measurement alignment method of the present invention. In this embodiment, the measurement alignment method 200 is applied to the temperature measuring device, and comprises following steps. In a step 201, the correspondence table, which records the first and second sensed distances and a measurement angle, is built in the micro processing unit 4 in advance. The correspondence table can be built by doing experiments in which the user operates the temperature measuring device at a correct position to measure temperature, to find a corresponding relationship between the tolerable measurement angle and the first and second sensed distances d1 and d2, as shown in FIG. 2, under the acceptable temperature measurement result. In a step 202, the micro processing unit 4 determines whether to execute the temperature measurement, for example, the micro processing unit 4 can determine according to the trigger signal of the button unit 5, if the button unit 5 is pressed to generate the trigger signal, the method proceeds a step 203; otherwise, the method proceeds the step 202 again. Furthermore, the micro processing unit 4 can also determine, according to the distance sensing signal of one of the first and second distance sensing units 1 and 2, whether to execute the temperature measurement. For example, the first distance sensing unit 1 is taken as example, and when the distance sensing signal outputted from the first distance sensing unit 1 is a distance sensing signal indicative of the predetermined distance d1, the method proceeds the step 203, otherwise, the method proceeds the determination operation again; or, the micro processing unit 4 can calculate the sensed distance according to the distance sensing signal outputted from the first distance sensing unit 1, and when the sensed distance is the same as the predetermined distance d1, the method proceeds a step 203, otherwise, the method proceeds the determination operation again. In the step 203, the micro processing unit 4 controls the first and second distance sensing units 1 and 2 to sense distance, and then receive the distance sensing signals outputted from the first and second distance sensing units 1 and 2, to calculate the first and second sensed distances.

Next, in a step 204, the micro processing unit 4 determines whether the first and second sensed distances meet the data recorded in the correspondence table, which can be served as a measurement execution condition, and if yes, the method proceeds the step 205; otherwise, the method is back to the step 203 to sense distance again. In the step 205, the micro processing unit 4 outputs the warning signal to the warning unit 6, for prompting the user that the operation of the temperature measuring device is correct, and also prompting the user to not shift the device, so as to avoid affecting the accuracy of the measured temperature. The warning unit 6 can be the LED device or the buzzer. In the step 206, the micro processing unit 4 controls the temperature sensing unit 3 to execute the temperature measurement, and find the corresponding measurement angle from the correspondence table according to the first and second sensed distances calculated in the step 203, and according to the temperature sensing signal of the temperature sensing unit 3 and the corresponding measurement angle, the micro processing unit 4 can calculate and store the temperature measurement value. In a step 207, the micro processing unit 4 outputs the temperature measurement value to the display unit 7 for displaying the temperature measurement value. Furthermore, in this embodiment, the order of the step 205, the step 206 and the step 207 is not limited; and the step 205, the step 206 and the step 207 can be executed in any order as long as the warning unit 6 prompts the user that the device is operated in the correct position after the micro processing unit 4 determines that the first and second sensed distances meet the date recorded in the correspondence table.

Figure 5:
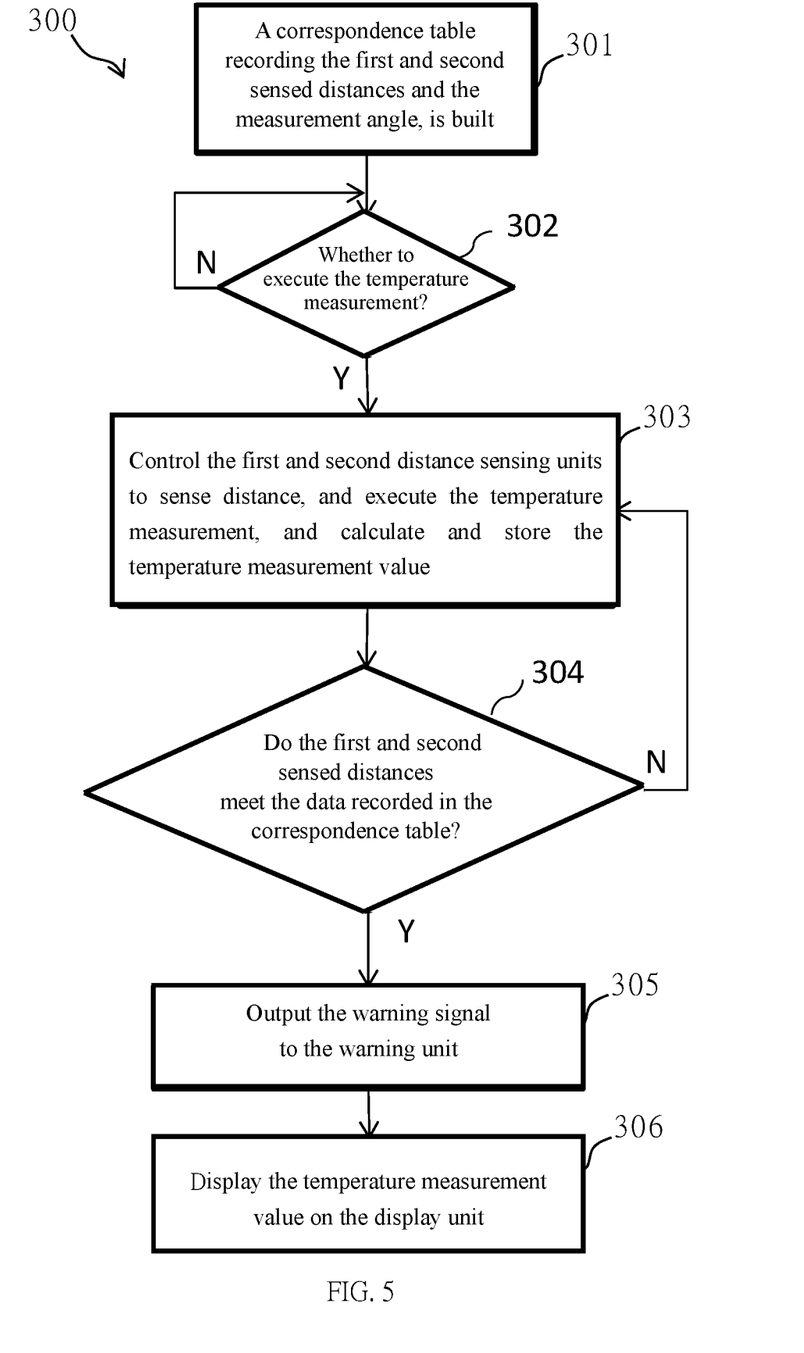
FIG. 5 is a flow chart of a third embodiment of a measurement alignment method of the present invention.

Please refer to FIG. 5, which shows a flow chart of a third embodiment of a measurement alignment method of the present invention. In this embodiment, the measurement alignment method 300 is applied to the temperature measuring device, and comprises following steps. In a step 301, the correspondence table, which records the first and second sensed distances and the measurement angle, is built in the micro processing unit 4. The correspondence table can be obtained by doing the experiment in which the user operates the temperature measuring device at the correct position to measure temperature, to find the corresponding relationship between the tolerable measurement angle and the first and second sensed distances d1 and d2 shown in FIG. 2, under the acceptable temperature measurement result. In a step 302, the micro processing unit 4 determines whether to execute the temperature measurement, and the micro processing unit 4 can determine according to the trigger signal of the button unit 5, if the button unit 5 is pressed to generate the trigger signal, the method proceeds a step 303, otherwise, the method proceeds the step 302 again. Furthermore, the micro processing unit 4 determine, according to the distance sensing signal of one of the first and second distance sensing units 1 and 2, whether to execute the temperature measurement. For example, the first distance sensing unit 1 is taken as example, and when the distance sensing signal outputted from the first distance sensing unit 1 is a distance sensing signal indicative of the predetermined distance d1, the method proceeds the step 303, otherwise, the method proceeds determination operation; or, the micro processing unit 4 can calculate the sensed distance according to the distance sensing signal outputted from the first distance sensing unit 1, and when the sensed distance is the same as the predetermined distance d1, the method proceeds the step 303, otherwise, the method proceeds the determination operation again. In the step 303, the micro processing unit 4 controls the first and second distance sensing units 1 and 2 to sense distance, and receives the distance sensing signals outputted from the first and second distance sensing units 1 and 2, and calculates the first and second sensed distances; next, the micro processing unit 4 executes the temperature measurement, and calculate and store the temperature measurement value according to the temperature sensing signal of the temperature sensing unit 3.

Next, in a step 304, the micro processing unit 4 determines whether the first and second sensed distances meet the data recorded in the correspondence table, which can be served as a measurement execution condition, and if yes, the method proceeds a step 305; otherwise, the method is back to the step 303 to continue the distance and temperature measurement. In the step 305, the micro processing unit 4 outputs the warning signal to the warning unit 6, for prompting the user that the temperature measuring device is operated in the correct position to measure the temperature. Preferably, the warning unit 6 can be the LED device or the buzzer. In a step 306, the micro processing unit 4 outputs the temperature measurement value to the display unit 7 for displaying the temperature measurement value.

Figure 6:
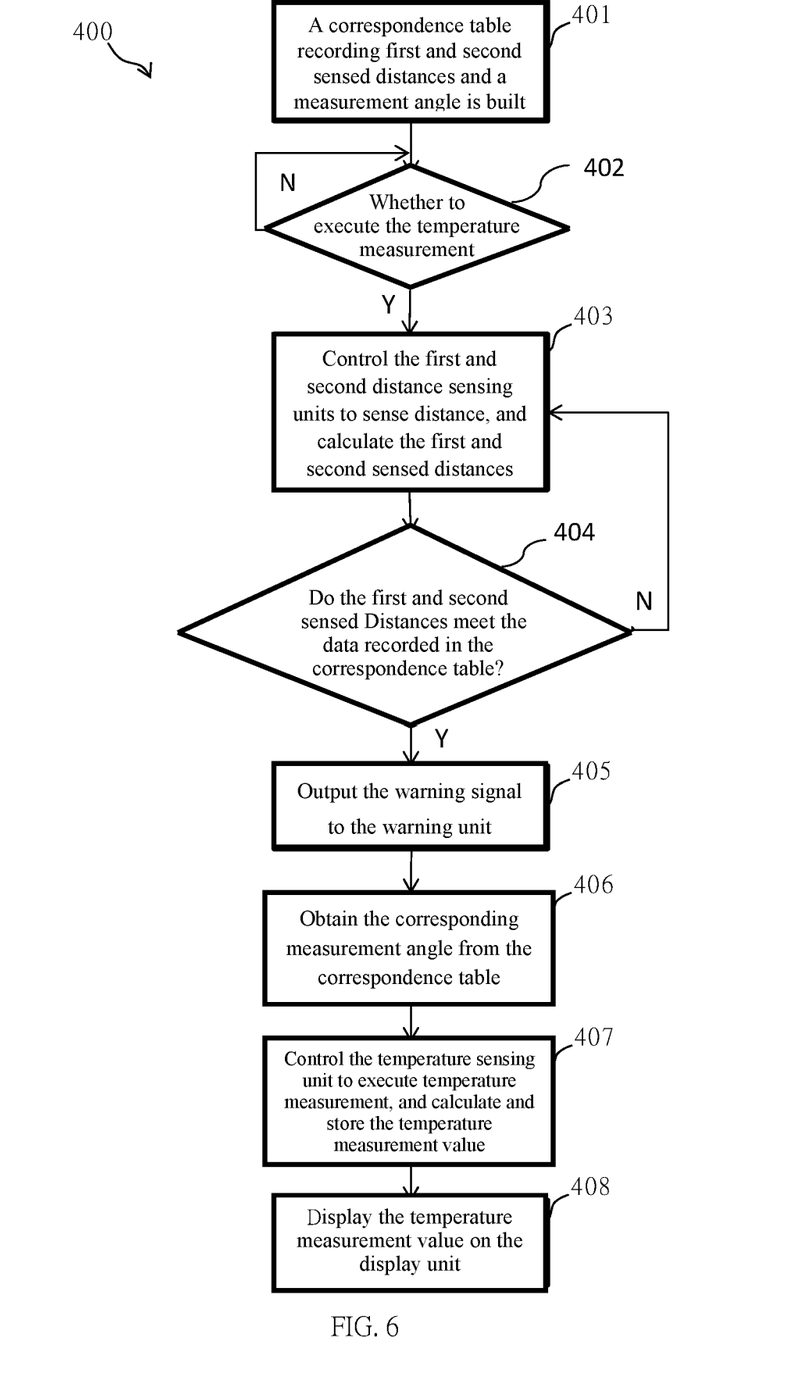
FIG. 6 is a flow chart of a fourth embodiment of a measurement alignment method of the present invention.

Please refer to FIG. 6, which shows a flow chart of a fourth embodiment of a measurement alignment method of the present invention. In this embodiment, the measurement alignment method 400 is applied to the temperature measuring device of the present invention, and comprises following steps. In a step 401, the correspondence table recording first and second sensed distances and a measurement angle, is built in the micro processing unit 4. The correspondence table can be obtained by doing experiment in which the user operates the temperature measuring device at a correct position to measure temperature, to find the corresponding relationship between the tolerable measurement angle and the first and second sensed distances d1 and d2 (as shown in FIG. 2) under the acceptable temperature measurement result. In a step 402, the micro processing unit 4 determines whether to execute the temperature measurement, the micro processing unit 4 can determine according to the trigger signal of the button unit 5, if the button unit 5 is pressed to generate the trigger signal, the method proceeds a step 403, otherwise, the method proceeds the step 402 again. Furthermore, the micro processing unit 4 can determine, according to the distance sensing signal of one of the first and second distance sensing units 1 and 2, whether to execute the temperature measurement. For example, the first distance sensing unit 1 is taken as example, when the distance sensing signal outputted from the first distance sensing unit 1 is a distance sensing signal indicative of predetermined distance d1, the method proceeds a step 403, otherwise, the method repeats the determination operation; or, the micro processing unit 4 can calculate the sensed distance according to the distance sensing signal outputted from the first distance sensing unit 1, and when the sensed distance is the same as the predetermined distance d1, the method proceeds a step 403, otherwise, the method repeats the determination operation. In a step 403, the micro processing unit 4 controls the first and second distance sensing units 1 and 2 to sense distance, and receive the distance sensing signals outputted from the first and second distance sensing units 1 and 2, and calculate the first and second sensed distances.

Next, in a step 404, the micro processing unit 4 determines whether the first and second sensed distances meet the data recorded in the correspondence table, which can be served as a measurement execution condition, and if yes, the method proceeds a step 405; otherwise, the method is back to the step 403 to continue the operation of sensing the distance. In the step 405, the micro processing unit 4 output the warning signal to the warning unit 6 for prompting the user that the operation of the temperature measuring device is correct and also prompting the user to not shift the device to avoid affecting the accuracy of the measured temperature. Preferably, the warning unit 6 can be the LED device or the buzzer. In the step 406, the micro processing unit 4 finds the corresponding measurement angle from the correspondence table according to the first and second sensed distances calculated in the step 403. In a step 407, the micro processing unit 4 controls the temperature sensing unit 3 to execute temperature measurement, and calculates and stores the temperature measurement value according to the temperature sensing signal of the temperature sensing unit 3. In a step 408, the micro processing unit 4 outputs the temperature measurement value to the display unit 7 for displaying the temperature measurement value.

Figure 7:
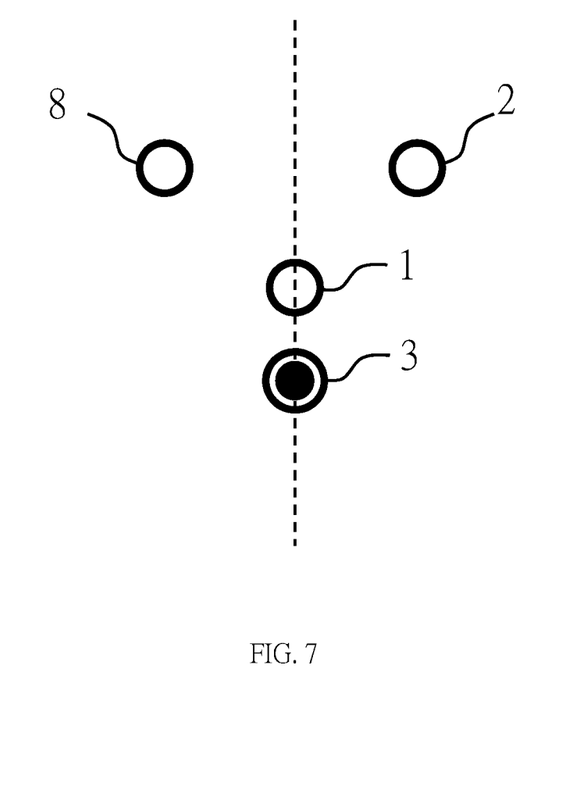
FIG. 7 is a front view of the temperature measuring device using three distance sensing units, according to the present invention.

Please refer to FIG. 7, which shows a front view of the temperature measuring device using three distance sensing units, according to the present invention. In this embodiment, the temperature measuring device can include a third distance sensing unit 8 electrically connected to the micro processing unit 4 and configured to output a third distance sensing signal. The micro processing unit 4 can calculate a first sensed distance, a second sensed distance and a third sensed distance according to the first distance sensing signal, the second distance sensing signal and the third distance sensing signal, respectively, and then can determine, according to the first sensed distance, the second sensed distance and the third sensed distance, whether the display unit 7 displays the calculated temperature measurement value according to the temperature sensing signal. The first distance sensing unit 1 and the temperature sensing unit 4 are positioned on an axis, and the second distance sensing unit 2 and the third distance sensing unit 8 are symmetrically on two sides of the axis, respectively, and the first distance sensing unit 1, the second distance sensing unit 2 and the third distance sensing unit 8 are arranged in an inverted-triangle. The configuration of the second distance sensing unit 2 and the third distance sensing unit 8 can improve the accuracy of measurement, to prevent the temperature measurement from being performed when the to-be-measured user's head is obliquely postured or the operator holds the temperature measuring device by an oblique posture, thereby ensuring the correct posture for temperature measurement.

Furthermore, as shown in FIG. 7, the first distance sensing unit 1 and the temperature sensing unit 3 are positioned on an axis, and the second distance sensing unit 2 and the third distance sensing unit 8 are symmetrically positioned on two sides of the axis, respectively. The distances d1, d2 and d3 indicate the distances sensed by the first distance sensing unit 1, the second distance sensing unit 2, and the third distance sensing unit 8, respectively. Under the measurement execution condition, the range of the distance d1, such as a range of 1 cm to 5 cm, is a distance range in which the measurement can be performed, and when the distance d2 is higher than the distance d3, it indicates that the operator holds the temperature measuring device by a rightwardly-deflecting posture, and when the distance d2 is lower than the distance d3, it indicates that the operator holds the temperature measuring device by a leftwardly-deflecting posture. For this reason, within a preset range of distance d1, the difference between the distance d2 and the distance d3, such as in a range of −0.5 cm to 0.5 cm, can be used to define a tolerable measurement angle, and the different distances d1, d2 and d3, and the tolerable measurement angle corresponding thereto can be collected in advance and recorded in the correspondence table for implementing the determination step 204 of FIG. 4, the determination step 304 of FIG. 5 and the determination step 404 of FIG. 6.

In the embodiment shown in FIG. 7, according to the step 103 shown in FIG. 3, the micro processing unit 4 can control the first distance sensing unit 1, the second distance sensing unit 2, and the third distance sensing unit 8 to measure distance, and can receive the distance sensing signals outputted from the first distance sensing unit 1, the second distance sensing unit 2, and the third distance sensing unit 8. In the step 104, the micro processing unit 4 determines whether the distance sensing signals of the first distance sensing unit 1, the second distance sensing unit 2, and the third distance sensing unit 8 match the measurement execution condition, and if yes, the step 105 is performed; otherwise, the step 103 is performed to continuously measure distance. The measurement execution condition can be set to include a first predetermined signal, a second predetermined signal and a third predetermined signal, or include a first predetermined signal range, a second predetermined signal range, and a third predetermined signal range, or include a first predetermined value, a second predetermined value and a third predetermined value, or include a first predetermined range, a second predetermined range, and a third predetermined range.

In the embodiment shown in FIG. 7, according to the step 201 shown in FIG. 4, the micro processing unit 4 stores a built-in correspondence table recording a first sensed distance, a second sensed distance, a third sensed distance, and a measurement angle. The correspondence table can be built by doing experiments in which the user operates the temperature measuring device at a correct position to measure temperature, to find a corresponding relationship between the tolerable measurement angle and the first, second and third distance sensing units 1, 2 and 8, as shown in FIG. 7. In the step 203, the micro processing unit 4 can control the first distance sensing unit 1, the second distance sensing unit 2, and the third distance sensing unit 8 to measure distance, to receive the distance sensing signals outputted from the first distance sensing unit 1, the second distance sensing unit 2, and the third distance sensing unit 8, and to calculate the first sensed distance, the second sensed distance and the third sensed distance according to the distance sensing signals. In the step 204, the micro processing unit 4 can determine whether the first sensed distance, the second sensed distance and the third sensed distance match the correspondence table, and if yes, the step 205 is performed; otherwise, the step 203 is performed to continuously measure distance.

In the embodiment as shown in FIG. 7, according to the step 301 shown in FIG. 5, the correspondence table, which records the first, second and third sensed distances and a measurement angle, is built in the micro processing unit 4 in advance. The correspondence table can be built by doing experiments in which the user operates the temperature measuring device at a correct position to measure temperature, to find a corresponding relationship between the tolerable measurement angle and the first, second and third distance sensing units 1, 2 and 8, as shown in FIG. 7. In the step 303, the micro processing unit 4 can control the first, second and third distance sensing units 1, 2 and 8 to measure distance, to receive the distance sensing signals outputted from the first, second and third distance sensing units 1, 2 and 8, and calculate the first, second and third sensed distances according to the distance sensing signals, and calculate and store a temperature measurement value according to the temperature sensing signal of the temperature sensing unit 3. In the step 304, the micro processing unit 4 can determine whether the first, second and third sensed distances match the correspondence table, and if yes, the step 305 is performed; otherwise, the step 303 is performed to continuously measure distance.

In the embodiment shown in FIG. 7, according to the step 401 shown in FIG. 6, the correspondence table, which records the first, second and third sensed distances and a measurement angle, is built in the micro processing unit 4 in advance. The correspondence table can be built by doing experiments in which the user operates the temperature measuring device at a correct position to measure temperature, to find a corresponding relationship between the tolerable measurement angle and the first, second and third distance sensing units 1, 2 and 8, as shown in FIG. 7. In the step 403, the micro processing unit 4 can control the first, second and third distance sensing units 1, 2 and 8 to measure distance, to receive the distance sensing signals outputted from the first, second and third distance sensing units 1, 2 and 8, and calculate the first, second and third sensed distances. In the step 404, the micro processing unit 4 can determine whether the first, second and third sensed distances match the correspondence table, and if yes, the step 405 is performed; otherwise, the step 403 is performed to continuously measure distance. In the step 406, the micro processing unit 4 search a measurement angle corresponding to the first, second and third sensed distances calculated in the step 403, from the correspondence table.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A temperature measuring device, comprising:
   a first distance sensing unit configured to output a first distance sensing signal and a second distance sensing unit configured to output a second distance sensing signal;
   a temperature sensing unit configured to output a temperature sensing signal;
   a display unit configured to display a temperature measurement value; and
   a microprocessor electrically connected to the first distance sensing unit, the second distance sensing unit, the temperature sensing unit, and the display unit, wherein the microprocessor receives the first distance sensing signal and the second distance sensing signal to detect a tilt angle of the temperature sensing unit, and according to a measurement execution condition that the tilt angle is a tolerable measurement angle, determines whether the display unit displays the temperature measurement value calculated according to the temperature sensing signal; wherein the tolerable measurement angle is determined by which the first distance sensing signal and the second distance sensing signal are respectively within a first predetermined signal range and a second predetermined signal range, or which a first sensed distance value and a second sensed distance value calculated according to the two distance sensing signals are respectively within a first predetermined range and a second predetermined range.

2. The temperature measuring device according to claim 1, further comprising a correspondence table recording the first sensed distance, the second sensed distance and a measurement angle, and the measurement execution condition is the correspondence table.

3. The temperature measuring device according to claim 1, wherein the first distance sensing unit, the second distance sensing unit and the temperature sensing unit are positioned on an axis.

4. The temperature measuring device according to claim 1, further comprising a third distance sensing unit which is electrically connected to the microprocessor and outputs a third distance sensing signal, wherein the microprocessor determines, according to the first distance sensing signal, the second distance sensing signal and the third distance sensing signal, whether the display unit displays the temperature measurement value calculated according to the temperature sensing signal.

5. The temperature measuring device according to claim 4, wherein the first distance sensing unit and the temperature sensing unit are positioned on an axis, and the second distance sensing unit and the third distance sensing unit are symmetrically positioned on two sides of the axis.

6. The temperature measuring device according to claim 4, wherein the microprocessor receives the first distance sensing signal, the second distance sensing signal, and the third distance sensing signal, and the tolerable measurement angle is determined by one of:
   that the three distance sensing signals are respectively within a first predetermined signal range, a second predetermined signal range and a third predetermined signal range, and
   that a first sensed distance value, a second sensed distance value and a third sensed distance value calculated according to the three distance sensing signals are respectively within a first predetermined range, a second predetermined range and a third predetermined range.

7. The temperature measuring device according to claim 6, further comprising a correspondence table recording the first sensed distance, the second sensed distance, the third sensed distance and a measurement angle, and the measurement execution condition is the correspondence table.

8. A measurement alignment method, applied to a temperature measuring device which comprises a display unit for displaying a temperature measurement value, wherein the method comprises:
   disposing a first distance sensing unit and a second distance sensing unit;
   enabling the first distance sensing unit and the second distance sensing unit, to obtain a first distance sensing signal and a second distance sensing signal respectively;
   detecting a tilt angle of the temperature sensing unit by the first distance sensing signal and the second distance sensing signal; and
   determining whether the display unit displays the temperature measurement value, according to a measurement execution condition that the tilt angle is a tolerable measurement angle, wherein the tolerable measurement angle is determined by:
   which the first distance sensing signal and the second distance sensing signal are respectively within a first predetermined signal range and a second predetermined signal range, or
   which a first sensed distance value and a second sensed distance value calculated according to the two distance sensing signals are respectively within a first predetermined range and a second predetermined range.

9. The measurement alignment method according to claim 8, further comprising:

comparing the first distance sensing signal, the second distance sensing signal, and the measurement execution condition; and determining whether the display unit displays the temperature measurement value calculated according to the temperature sensing signal.

10. The measurement alignment method according to claim 8, further comprising a correspondence table recording the first sensed distance, the second sensed distance and a measurement angle, and the measurement execution condition is the correspondence table.

11. The measurement alignment method according to claim 8, further comprising:

disposing a third distance sensing unit; and enabling the third distance sensing unit to obtain a third distance sensing signal.

12. The measurement alignment method according to claim 11, further comprising:

detecting the tilt angle of the temperature sensing unit by the first distance sensing signal, the second distance sensing signal and the third distance sensing signal;

determining whether the display unit displays the temperature measurement value, according to the measurement execution condition that the tilt angle is the tolerable measurement angle, wherein the tolerable measurement angle is determined by:

which the three distance sensing signals are respectively within a first predetermined signal range, a second predetermined signal range and a third predetermined signal range, or which a first sensed distance value, a second sensed distance value and a third sensed distance value calculated according to the three distance sensing signals are respectively within a first predetermined range, a second predetermined range and a third predetermined range.

* * * * *